United States Patent
Rousseau et al.

(10) Patent No.: US 9,161,855 B2
(45) Date of Patent: Oct. 20, 2015

(54) TISSUE SUPPORTING DEVICE AND METHOD

(75) Inventors: Robert A. Rousseau, Ottsville, PA (US); David C. Lindh, Sr., Flemington, NJ (US)

(73) Assignee: ETHICON, INC., Somerville, NJ (US)

( * ) Notice: Subject to any disclaimer, the term of this patent is extended or adjusted under 35 U.S.C. 154(b) by 934 days.

(21) Appl. No.: 13/279,384

(22) Filed: Oct. 24, 2011

(65) Prior Publication Data

US 2013/0098371 A1    Apr. 25, 2013

(51) Int. Cl.
*A61F 5/56*    (2006.01)

(52) U.S. Cl.
CPC ..................... *A61F 5/566* (2013.01)

(58) Field of Classification Search
CPC ... A61F 5/566; A61F 5/56; A61F 2201/0038; A61F 2/20; A61F 2250/0004; A61F 2/00; A61F 2/02; A61F 4/00; A24C 5/474; A44B 9/10; A61B 13/00; A61B 19/203; A61B 2019/204; A62B 9/022; B63C 11/2227; G04B 37/14; G04B 37/1486; A61N 1/0548; A61N 1/3601; A61M 16/0488; A61M 16/0493; A61M 19/00; A61M 2202/0208; A61M 2210/0643; A61M 2210/0656; A61M 2202/064; A61M 15/0028; A61M 15/0043; A61M 15/0021; A61M 15/0091; A61M 15/0045; A61M 15/0048; A61M 15/0086; A61M 15/06; A61M 2205/6081; A61M 2206/16; A61M 2205/8206; A61M 15/00; Y10S 602/902
USPC ................. 128/848, 858–862; 602/902; 433/6
See application file for complete search history.

(56) References Cited

U.S. PATENT DOCUMENTS

| | | | |
|---|---|---|---|
| 2,705,492 A | * | 4/1955 | Chandler ..................... 128/862 |
| 3,123,077 A | | 3/1964 | Alcamo |
| 3,378,010 A | | 4/1968 | Codling et al. |
| 4,024,855 A | | 5/1977 | Bucalo |
| 4,069,825 A | | 1/1978 | Akiyama |

(Continued)

FOREIGN PATENT DOCUMENTS

| | | |
|---|---|---|
| CN | 2465680 | 12/2001 |
| CN | 201029957 Y | 3/2008 |

(Continued)

OTHER PUBLICATIONS

Database WPI Week 198312, Thomson Scientific, London, GB; AN 1983-D9513K XP002693421.

(Continued)

*Primary Examiner* — Michael Brown

(57) ABSTRACT

A tissue supporting device is provided and method of use. The device includes an anchor element having a plate-like element and first and second side walls extending upwardly therefrom. The plate-like element is defined by front and rear edges, and first and second side edges, with the rear edge being longer than the front edge. The first and second side walls are aligned substantially along at least a portion of the first and second side edges of the plate-like element such that a distance between the first and second side walls at a front side is less than a distance between the first and second side walls at a rear side. The device also includes a soft tissue supporting element adapted for engaging and supporting soft tissue. The soft tissue supporting element is coupled to the plate-like element and extends outwardly from the anchor element.

6 Claims, 11 Drawing Sheets

(56) References Cited

U.S. PATENT DOCUMENTS

| | | | |
|---|---|---|---|
| 4,290,763 A | 9/1981 | Hurst | |
| 4,523,584 A | 6/1985 | Yachia et al. | |
| 4,557,264 A | 12/1985 | Hinsch | |
| 4,839,215 A | 6/1989 | Starling et al. | |
| 4,881,939 A | 11/1989 | Newman | |
| 4,950,285 A | 8/1990 | Wilk | |
| 5,053,047 A | 10/1991 | Yoon | |
| 5,067,485 A | 11/1991 | Cowen | |
| 5,123,913 A | 6/1992 | Wilk et al. | |
| 5,192,271 A | 3/1993 | Kalb et al. | |
| 5,192,274 A | 3/1993 | Bierman | |
| 5,269,783 A | 12/1993 | Sander | |
| 5,284,161 A | 2/1994 | Karell | |
| 5,311,028 A | 5/1994 | Glavish | |
| 5,393,984 A | 2/1995 | Glavish | |
| 5,483,077 A | 1/1996 | Glavish | |
| 5,484,444 A | 1/1996 | Braunschweiler et al. | |
| 5,609,559 A | 3/1997 | Weitzner | |
| 5,683,417 A | 11/1997 | Cooper | |
| 5,704,895 A | 1/1998 | Scott et al. | |
| 5,792,067 A | 8/1998 | Karell | |
| 5,843,077 A | 12/1998 | Edwards | |
| 5,931,855 A | 8/1999 | Buncke | |
| 6,161,541 A | 12/2000 | Woodson | |
| 6,190,401 B1 | 2/2001 | Green et al. | |
| 6,241,747 B1 | 6/2001 | Ruff | |
| 6,250,307 B1 | 6/2001 | Conrad et al. | |
| 6,348,156 B1 | 2/2002 | Vishnoi et al. | |
| 6,408,851 B1 * | 6/2002 | Karell | 128/848 |
| 6,431,174 B1 | 8/2002 | Knudson et al. | |
| 6,432,437 B1 | 8/2002 | Hubbard | |
| 6,457,472 B1 | 10/2002 | Schwartz et al. | |
| 6,513,530 B2 | 2/2003 | Knudson et al. | |
| 6,523,542 B2 | 2/2003 | Knudson et al. | |
| 6,578,580 B2 | 6/2003 | Conrad et al. | |
| 6,589,549 B2 | 7/2003 | Shih et al. | |
| 6,599,310 B2 | 7/2003 | Leung et al. | |
| 6,627,600 B2 | 9/2003 | Boutignon | |
| 6,634,362 B2 | 10/2003 | Conrad et al. | |
| 6,638,284 B1 | 10/2003 | Rousseau et al. | |
| 6,716,251 B1 | 4/2004 | Asius et al. | |
| 6,742,524 B2 | 6/2004 | Knudson et al. | |
| 6,755,868 B2 | 6/2004 | Rousseau | |
| 6,800,082 B2 | 10/2004 | Rousseau | |
| 6,899,105 B2 | 5/2005 | Krueger et al. | |
| 6,955,172 B2 | 10/2005 | Nelson et al. | |
| 6,981,944 B2 | 1/2006 | Jamiolkowski et al. | |
| 7,017,582 B2 | 3/2006 | Metzger et al. | |
| 7,056,331 B2 | 6/2006 | Kaplan et al. | |
| 7,135,189 B2 | 11/2006 | Knapp | |
| 7,146,981 B2 | 12/2006 | Knudson et al. | |
| 7,166,570 B2 | 1/2007 | Hunter et al. | |
| 7,213,599 B2 | 5/2007 | Conrad et al. | |
| 7,237,554 B2 | 7/2007 | Conrad et al. | |
| 7,261,702 B1 | 8/2007 | Alexandre et al. | |
| 7,288,075 B2 | 10/2007 | Parihar et al. | |
| 7,297,102 B2 | 11/2007 | Smith et al. | |
| 7,322,993 B2 | 1/2008 | Metzger et al. | |
| 7,337,781 B2 | 3/2008 | Vassallo | |
| 7,360,432 B2 | 4/2008 | Lehtonen | |
| 7,360,542 B2 | 4/2008 | Nelson et al. | |
| 7,367,340 B2 | 5/2008 | Nelson et al. | |
| 7,401,611 B2 | 7/2008 | Conrad et al. | |
| 7,442,389 B2 | 10/2008 | Quelle et al. | |
| 7,601,164 B2 | 10/2009 | Wu | |
| 7,669,603 B2 | 3/2010 | Knudson et al. | |
| 7,806,908 B2 | 10/2010 | Ruff | |
| 7,850,894 B2 | 12/2010 | Lindh, Sr. et al. | |
| 7,857,829 B2 | 12/2010 | Kaplan et al. | |
| 7,888,119 B2 | 2/2011 | Sugaya et al. | |
| 8,142,422 B2 | 3/2012 | Makower et al. | |
| 8,413,661 B2 | 4/2013 | Rousseau et al. | |
| 8,728,143 B2 | 5/2014 | Seguin et al. | |
| 8,800,567 B2 | 8/2014 | Weadock et al. | |
| 2001/0037133 A1 | 11/2001 | Knudson et al. | |
| 2002/0144685 A1 | 10/2002 | Ivanovich et al. | |
| 2003/0004579 A1 | 1/2003 | Rousseau et al. | |
| 2003/0034312 A1 | 2/2003 | Unger et al. | |
| 2003/0149445 A1 | 8/2003 | Knudson et al. | |
| 2003/0149447 A1 | 8/2003 | Morency et al. | |
| 2003/0149488 A1 | 8/2003 | Metzger et al. | |
| 2003/0176875 A1 | 9/2003 | Anderson et al. | |
| 2004/0020492 A1 | 2/2004 | Dubrul et al. | |
| 2004/0020498 A1 | 2/2004 | Knudson et al. | |
| 2004/0028676 A1 | 2/2004 | Klein et al. | |
| 2004/0044366 A1 | 3/2004 | Bonutti et al. | |
| 2004/0102796 A1 | 5/2004 | Hill et al. | |
| 2004/0139975 A1 | 7/2004 | Nelson et al. | |
| 2004/0144395 A1 | 7/2004 | Evans et al. | |
| 2004/0147811 A1 | 7/2004 | Diederich et al. | |
| 2004/0149290 A1 | 8/2004 | Nelson et al. | |
| 2004/0153127 A1 | 8/2004 | Gordon et al. | |
| 2004/0231678 A1 | 11/2004 | Fierro | |
| 2005/0038472 A1 | 2/2005 | Furst | |
| 2005/0082452 A1 | 4/2005 | Kirby | |
| 2005/0092334 A1 | 5/2005 | Conrad et al. | |
| 2005/0115572 A1 | 6/2005 | Brooks et al. | |
| 2005/0121039 A1 | 6/2005 | Brooks et al. | |
| 2005/0159637 A9 | 7/2005 | Nelson et al. | |
| 2005/0165352 A1 | 7/2005 | Henry et al. | |
| 2005/0199248 A1 | 9/2005 | Pflueger et al. | |
| 2005/0203576 A1 | 9/2005 | Sulamanidze et al. | |
| 2005/0251255 A1 | 11/2005 | Metzger et al. | |
| 2005/0267321 A1 | 12/2005 | Shadduck | |
| 2005/0267531 A1 | 12/2005 | Ruff et al. | |
| 2005/0267532 A1 | 12/2005 | Wu | |
| 2005/0267571 A1 | 12/2005 | Spence et al. | |
| 2005/0279365 A1 | 12/2005 | Armijo et al. | |
| 2006/0005843 A9 | 1/2006 | Nelson et al. | |
| 2006/0079935 A1 | 4/2006 | Kolster | |
| 2006/0083767 A1 | 4/2006 | Deusch et al. | |
| 2006/0093644 A1 | 5/2006 | Quelle et al. | |
| 2006/0150986 A1 | 7/2006 | Roue et al. | |
| 2006/0185673 A1 | 8/2006 | Critzer et al. | |
| 2006/0206197 A1 | 9/2006 | Morsi | |
| 2006/0207608 A1 | 9/2006 | Hirotsuka et al. | |
| 2006/0207612 A1 | 9/2006 | Jackson et al. | |
| 2006/0228391 A1 | 10/2006 | Seyedin et al. | |
| 2006/0241339 A1 | 10/2006 | Cook et al. | |
| 2006/0266369 A1 | 11/2006 | Atkinson et al. | |
| 2006/0289015 A1 | 12/2006 | Boucher et al. | |
| 2007/0000497 A1 | 1/2007 | Boucher et al. | |
| 2007/0005109 A1 | 1/2007 | Popadiuk et al. | |
| 2007/0005110 A1 | 1/2007 | Collier et al. | |
| 2007/0102004 A1 | 5/2007 | Nelson et al. | |
| 2007/0102010 A1 | 5/2007 | Lemperle et al. | |
| 2007/0110788 A1 | 5/2007 | Hissong et al. | |
| 2007/0119463 A1 | 5/2007 | Nelson et al. | |
| 2007/0123996 A1 | 5/2007 | Sugaya et al. | |
| 2007/0144531 A1 | 6/2007 | Tomas et al. | |
| 2007/0144534 A1 | 6/2007 | Mery et al. | |
| 2007/0144535 A1 | 6/2007 | Hegde et al. | |
| 2007/0190108 A1 | 8/2007 | Datta et al. | |
| 2007/0204866 A1 | 9/2007 | Conrad et al. | |
| 2007/0209665 A1 | 9/2007 | Gillis et al. | |
| 2007/0227545 A1 | 10/2007 | Conrad et al. | |
| 2007/0233276 A1 | 10/2007 | Conrad et al. | |
| 2007/0246052 A1 | 10/2007 | Hegde et al. | |
| 2007/0256693 A1 | 11/2007 | Paraschac et al. | |
| 2007/0257395 A1 | 11/2007 | Lindh et al. | |
| 2007/0261701 A1 | 11/2007 | Sanders | |
| 2007/0267027 A1 | 11/2007 | Nelson et al. | |
| 2007/0270631 A1 | 11/2007 | Nelson et al. | |
| 2007/0272257 A1 | 11/2007 | Nelson et al. | |
| 2007/0288057 A1 | 12/2007 | Kuhnel | |
| 2007/0295338 A1 | 12/2007 | Loomas et al. | |
| 2007/0295340 A1 | 12/2007 | Buscemi | |
| 2008/0023012 A1 | 1/2008 | Dineen et al. | |
| 2008/0035158 A1 | 2/2008 | Pflueger et al. | |
| 2008/0035160 A1 | 2/2008 | Woodson et al. | |
| 2008/0066764 A1 | 3/2008 | Paraschac et al. | |
| 2008/0066765 A1 | 3/2008 | Paraschac et al. | |
| 2008/0066767 A1 | 3/2008 | Paraschac et al. | |
| 2008/0066769 A1 | 3/2008 | Dineen et al. | |

(56) References Cited

U.S. PATENT DOCUMENTS

| | | |
|---|---|---|
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau et al. |
| 2010/0030011 A1 | 2/2010 | Weadock et al. |
| 2010/0037901 A1 | 2/2010 | Rousseau et al. |
| 2010/0080791 A1 | 4/2010 | Rousseau et al. |
| 2010/0106246 A1 | 4/2010 | Rousseau et al. |
| 2010/0108077 A1 | 5/2010 | Lindh et al. |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1 | 6/2010 | Puisais |
| 2010/0163056 A1 | 7/2010 | Tschopp et al. |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh, Sr. et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1 | 9/2011 | Frank |
| 2011/0245850 A1 | 10/2011 | van der Burg et al. |
| 2012/0123449 A1 | 5/2012 | Schaller et al. |
| 2012/0160249 A1* | 6/2012 | Thomason et al. ............ 128/848 |
| 2012/0245629 A1 | 9/2012 | Gross et al. |
| 2013/0098371 A1 | 4/2013 | Rousseau et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadock et al. |
| 2013/0319427 A1 | 12/2013 | Sung et al. |

FOREIGN PATENT DOCUMENTS

| | | |
|---|---|---|
| CN | 102198010 A | 9/2011 |
| DE | 10245076 A1 | 4/2004 |
| EP | 2145587 A2 | 1/2010 |
| EP | 2386252 A1 | 11/2011 |
| EP | 2517633 A1 | 10/2012 |
| FR | 2651113 A1 | 3/1991 |
| JP | 2001-145646 | 5/2001 |
| JP | 2003265621 | 9/2003 |
| RU | 2005447 C1 | 1/1994 |
| SU | 927236 B | 5/1982 |
| SU | 1697792 A1 | 12/1991 |
| WO | WO 97/13465 A1 | 4/1997 |
| WO | WO 99/00058 A1 | 1/1999 |
| WO | WO 00/66050 | 11/2000 |
| WO | WO 01/21107 A1 | 3/2001 |
| WO | WO 03/096928 A1 | 11/2003 |
| WO | WO 2004/016196 A2 | 2/2004 |
| WO | WO 2004/016196 A3 | 2/2004 |
| WO | WO 2004/020492 | 3/2004 |
| WO | WO 2004/021869 A2 | 3/2004 |
| WO | WO 2004/021870 A2 | 3/2004 |
| WO | WO 2004/021870 A3 | 3/2004 |
| WO | WO 2004/060311 A2 | 7/2004 |
| WO | WO 2004/060311 A3 | 7/2004 |
| WO | WO 2004/084709 A2 | 10/2004 |
| WO | WO 2004/084709 A3 | 10/2004 |
| WO | 2004/103196 A1 | 12/2004 |
| WO | WO 2005/046554 A2 | 5/2005 |
| WO | WO 2005/046554 A3 | 5/2005 |
| WO | WO 2005/051292 A2 | 6/2005 |
| WO | WO 2005/082452 A1 | 9/2005 |
| WO | WO 2005/122954 A1 | 12/2005 |
| WO | WO 2006/012188 A1 | 2/2006 |
| WO | WO 2006/072571 A1 | 7/2006 |
| WO | WO 2006/108145 A1 | 10/2006 |
| WO | WO 2007/056583 A1 | 5/2007 |
| WO | WO 2007/075394 A2 | 7/2007 |
| WO | WO 2007/075394 A3 | 7/2007 |
| WO | WO 2007/132449 A2 | 11/2007 |
| WO | WO 2007/132449 A3 | 11/2007 |
| WO | WO 2007/134005 A1 | 11/2007 |
| WO | WO 2007/146338 A2 | 12/2007 |
| WO | WO 2007/149469 A2 | 12/2007 |
| WO | WO 2007/149469 A3 | 12/2007 |
| WO | WO 2008/118913 A2 | 10/2008 |
| WO | WO 2009/023256 A2 | 10/2008 |
| WO | WO 2009/036094 A2 | 2/2009 |
| WO | WO 2010/065341 A2 | 3/2009 |
| WO | WO 2010/065341 A3 | 3/2009 |
| WO | WO 2010/019376 A2 | 2/2010 |
| WO | WO 2010/035303 A1 | 4/2010 |
| WO | WO 2012/004758 | 1/2012 |
| WO | WO 2012/041205 A1 | 4/2012 |
| WO | WO 2012/064902 A2 | 5/2012 |
| WO | WO 2012/170468 | 12/2012 |

OTHER PUBLICATIONS

U.S. Appl. No. 13/486,293, filed Jun. 1, 2012.
International Search Report dated Apr. 2, 2013 for International Patent Application No. PCT/US2012/067708.
Written Opinion dated Nov. 27, 2012 for International Patent Application No. PCT/US2012/056577.
Medtronic AIRvance System for Obstructive Sleep Apnea http://www.medtronic.com/for-healthcare-professionals/products-therapies/ear-nose-throat/sleep-disordered-breathing-products/airvance-system-for-obstructive-sleep-apnea/index.htm.
U.S. Appl. No. 13/307,482, filed Nov. 30, 2011.
Cole et al., "Snoring: A Review and a Reassessment", J. of Otolaryngology, vol. 24, No. 5 pp. 303-306 (1995).
Harries et al., "The Surgical treatment of snoring", J. of Laryngology and Otology, vol. 110, Issue 12 pp. 1105-1106 (1996).
Huang et al., "Biomechanics of snoring", Endeavour, vol. 19(3): pp. 96-100 (1995).
Pang, Kenny et al., "Tongue Suspension Suture in Obstructive Sleep Apnea", Operative Techniques in Otolaryngology, vol. 17, No. 4, pp. 252-256 (2006).
Repose Genioglossus Advancement, Influent Medical, www.influent.com, 1 page (2008).
Schleef et al., "Cytokine Activation of Vascular Endothelium, Effects on Tissue-Type 1 Plasminogen Activator Inhibitor" the J. of Biological Chem., vol. 263, No. 12, pp. 5797-5803 (1988).
Schwab et al., "Upper airway and soft tissue changes induced by CPAP in normal subject", Am. J. Respit. Crit. Care Med., vol. 154, No. 4 pp. 1106-1116 (1996).
Schwartz et al., "Effects of electrical stimulation to the soft palate on snoring and obstructive sleep apnea", J. Prosthetic Dentistry, vol. 76 pp. 273-281 (1996).
Shamsuzzaman et al., "Obstructive Sleep Apnea; Implications for Cardiac and Vascular Disease", JAMA vol. 290, No. 14 pp. 1906-1914 (2003).
Teles et al., "Use of Palatal Lift Prosthesis on Patient Submitted to Maxillectomy: A Case Report", Applied Cancer Res. vol. 25(3), pp. 151-154 (2005).
The Advance System, Aspire Medical, Inc. www.aspiremedical.com, 3 pp (2008).
The Pillar Procedure, Restore Medical, Inc. www.restoremedical.com, 2 pp (2008).
Vicente et al., "Tongue-Base Suspension in Conjunction with Uvulopapatopharyngoplasty for Treatment of Severe Obstructive

(56) References Cited

OTHER PUBLICATIONS

Sleep Apnea: Long-term Follow-Up Results", The Laryngoscope, vol. 116 pp. 1223-1227 (2006).
Wassmuth et al., "Cautery-assisted palatal stiffening operation for the treatment of obstructive sleep apnea syndrome", Otolaryngology—Head and Neck Surgery, vol. 123, pp. 55-60 (2000).
Wiltfang et al., "First results on daytime submandibular electrostimulation of suprahyoidal muscles to prevent night-time hypopharyngeal collapse in obstructive sleep apnea syndrome", Intl J. of Oral & Maxillofacial Surgery vol. 28 pp. 21-25 (1999).
U.S. Appl. No. 12/182,402, filed Jul. 30, 2008.
U.S. Appl. No. 12/183,955, filed Jul. 31, 2008.
U.S. Appl. No. 12/228,681, filed Aug. 14, 2008.
U.S. Appl. No. 12/238,991, filed Sep. 26, 2008.
U.S. Appl. No. 12/257,563, filed Oct. 24, 2008.
U.S. Appl. No. 12/261,102, filed Oct. 30, 2008.
U.S. Appl. No. 12/325,350, filed Dec. 1, 2008.
U.S. Appl. No. 12/378,573, filed Feb. 17, 2009.
U.S. Appl. No. 12/402,631, filed Mar. 12, 2009.
U.S. Appl. No. 13/247,713, filed Sep. 28, 2011.
U.S. Appl. No. 13/314,704, filed Dec. 8, 2011.
Notification of Transmittal of the International Search Report and the Written Opinion of the International Search Authority or the Declaration mailed on Feb. 3, 2010 for PCT/US2009/051921; International Filing Date: Jul. 28, 2009.
Notification of Transmittal of the International Search Report and the Written Opinion of the International Search Authority or the Declaration mailed on May 25, 2010 for PCT/US2010/023152; International Filing Date: Apr. 2, 2010.
International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Dec. 29, 2009 for International Patent Application No. PCT/US2009/061455.
International Search Report dated Apr. 29, 2010 for International Patent Application No. PCT/US2009/065293.
International Search Report dated Jan. 21, 2010 for International Patent Application No. PCT/US2009/052110.
International Search Report dated May 25, 2010 for International Patent Application No. PCT/US2010/023152.
International Search Report dated May 25, 2010 for International Patent Application No. PCT/US2010/025778.
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
International Search Report dated Apr. 9, 2013 for International Patent Application No. PCT/US2012/061569.

\* cited by examiner

TISSUE SUPPORTING DEVICE AND METHOD

FIELD OF THE INVENTION

The present invention relates generally to the field of medical devices, and more particularly to medical devices adapted to support soft tissue, with particular application for supporting or suspending the tongue from the mandible to treat sleep apnea conditions.

BACKGROUND

Obstructive sleep apnea (OSA) is a medical condition that is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and motor vehicle crashes. Despite the seriousness of OSA, a general lack of awareness among the public and healthcare professionals results in the vast majority of OSA sufferers remaining undiagnosed and untreated.

In the human body, the air filled space between the nasal cavity and the larynx is referred to as the upper airway. The most critical part of the upper airway associated with sleep disorders is the pharynx. The pharynx has three different anatomical levels. The nasopharynx is the upper portion of the pharynx located in the back of the nasal cavity. The oropharynx is the intermediate portion of the pharynx containing the soft palate, the epiglottis, and the curve at the back of the tongue. The hypopharynx is the lower portion of the pharynx located below the soft tissue of the oropharynx. The oropharynx is the section of the pharynx that is most likely to collapse due to the high prevalence of soft tissue structure, which leaves less space for airflow. The hypopharynx lies below the aperture of the larynx and behind the larynx, and extends to the esophagus.

As is well known to those skilled in the art, the soft palate and the tongue are both flexible structures. The soft palate provides a barrier between the nasal cavity and the mouth. In many instances, the soft palate is longer than necessary and it extends a significant distance between the back of the tongue and the posterior pharyngeal wall.

Although the muscles relax throughout the body during sleep, most of the muscles of the respiratory system remain active. During inhalation, the diaphragm contracts and causes negative pressure to draw air into the nasal cavity and mouth. The air then flows past the pharynx, through the trachea and into the lungs. The negative pressure causes the tissue of the upper airway to deform slightly, which narrows the airway passage. In apneic patients, the soft palate, the tongue, and/or the epiglottis collapse against the posterior pharyngeal wall to block airflow into the trachea. As the airway narrows, airflow through the pharynx becomes turbulent which causes the soft palate to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep. If apnea or hypopnea occurs more than five times per hour, most medical personnel diagnose the individual as having an upper airway resistance problem. Many of these patients exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

When an individual is awake, the back of the tongue and the soft palate maintain their shape and tone due to their respective internal muscles. As a result, the airway through the pharynx remains open and unobstructed. During sleep, however, the muscle tone decreases and the posterior surface of the tongue and the soft palate become more flexible and distensible. Without normal muscle tone to keep their shape and to keep them in place either alone or as a group, the posterior surface of the tongue, the epiglottis, and the soft palate SP tend to easily collapse to block the airway.

One known treatment, commonly referred to as continuous positive airway pressure (CPAP), is currently the "gold standard" for treating OSA and operates by delivering air into a patient's airway through a specially designed nasal mask or pillow. The flow of air creates positive pressure when the patient inhales to keep the airway open. Although CPAP is considered by many to be an effective non-surgical treatment for the alleviation of snoring and obstructive sleep apnea, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have problems. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Surgical implants have also been used to treat OSA. One such implant system, sold under the name AIRvance by Medtronic, Inc. of Minneapolis, Minn., uses a titanium screw that is inserted into the posterior aspect of the mandible at the floor of the mouth. A loop of suture is passed through the tongue base and attached to the mandibular bone screw. The procedure achieves a suspension or hammock of the tongue base making it less likely for the base of the tongue to prolapse during sleep. The use of the screw style bone anchor increases the risk of damage to the teeth or the nerve roots and or vasculature for the teeth.

Another known tongue suspension device similarly utilizes a bone screw in the mandible, but has the advantage of being adjustable. The device utilizes a flexible shape memory anchor within the tongue that is shaped similar to a grappling hook to engage the tissue within the tongue base. It is placed through a small incision in the sub-mental region and the suture is attached to a spool-like component attached to the mandible. Two to four weeks after healing, a small incision is made under the chin and a screw is turned to tighten the suture, thus pulling the device forward. While the device provides a simplified installation technique from within the sterile space, the anchors suffered from a high rate of device fracture and failure due to loading within the tongue musculature. Additionally, the risk of damage to the teeth or the nerve roots for the teeth is similar in both devices.

U.S. Pat. No. 7,367,340 describes the use of an element that is anchored to the mandible and is capable of applying force within the tongue to prevent the tongue from collapsing during sleep. In the embodiments described, the device consists of an element that is attached to the mandible though drilling of the mandible to provide a rigid point of fixation. The method of attachment produces essentially the same risk to the dental anatomy and nerve structures within the mandible.

This risk of damage by the above-described devices is illustrated by FIG. 1, which shows the typical mandible placement of a bone screw with a suspension fiber. As the screw extends into the mandible as shown, it may potentially strike the nerves, vasculature or teeth depending upon placement.

In order to avoid the risk of damage to the bone or nerves, an alternative approach that utilizes a flexible soft tissue anchor is illustrated in FIG. 2. In this embodiment, the anchor for the suspension loop is placed within the soft tissue of the sub-mental region and the suspension element is fixed to the soft flexible anchor. While this method avoids the issues associated with the placement of a bone anchor or screw in the mandible, it results in a more vertical angle $\theta_2$ of fixation for the suspension loop. When comparing the foregoing illustrations, it can be seen that the angle $\theta_2$ is larger for the soft tissue anchor system than the angle $\theta_1$ for the bone anchor device. It is possible that the anchor, if placed to far posterior to the infra-mandibular margin, may result in a vertical compression of the tongue base instead of anterior displacement of the tongue. Therefore, it is desirable to provide an anchor system that more closely approximates the resultant angle of suspension.

Given the disadvantages described above, there remains a need for a tongue suspension device that provides a point of fixation relative to the mandible, that can effectively resist motion due to loading of the musculature of the tongue during swallowing and speech, and that does not damage the boney structures or nerves of the mandible.

SUMMARY OF THE INVENTION

A tissue supporting device is provided having an anchor element having a plate-like element and first and second side walls extending upwardly therefrom. The plate-like element is defined by front and rear edges, and first and second side edges, and a length of the rear edge is longer than a length of the front edge. The first and second side walls are aligned substantially along at least a portion of the first and second side edges of the plate-like element such that a distance between the first and second side walls at a front side of the plate-like element is less than a distance between the first and second side walls at a rear side of the plate-like element. The tissue supporting device further includes a soft tissue supporting element adapted for engaging and supporting soft tissue that is coupled to the flat plate, and extends outwardly from the anchor element.

The soft tissue supporting element may be a looped filamentary element, and the plate-like element may includes one or more apertures therethrough, with the filamentary element being coupled to the plate-like element by passing through said one or more apertures.

In another embodiment, the tissue supporting device further includes a clamp element coupled to the anchor element so as to fixedly secure the filamentary element thereto, which may further be removably coupled thereto.

In yet another embodiment, the filamentary element is made of a material selected from the group consisting of polypropylene, ePTFE, polyamide, fibers produced from fluoropolymers, polyesters, polyolefins, urethanes, Poly (hexafluoropropylene-VDF) and polyaryletherketones.

In yet another embodiment, the anchor element is sized and shaped to engage a lower edge of an anterior portion of a mandible of a patient such that when so engaged, the anchor element straddles an anterior/inferior margin of the mandible with the front edge positioned substantially along a front edge of the mandible, the rear edge is positioned more rearward on the mandible, and the first and second side walls engage lateral outer edges of the mandible.

The soft tissue supporting device may further be adapted to be implanted within a patient's tongue so as to support the tongue from the anchor element.

In yet another embodiment, the anchor element further includes an anterior projection element projecting upwardly from a front side of the anchor element, and in yet another embodiment the tissue supporting device further includes an adjustment mechanism for adjusting a position of the first and second side walls relative to the plate-like element.

Also provided is a device for treating obstructive sleep apnea in a human patient having a mandible and a tongue including an anchor element having a plate-like element sized and shaped to straddle a lower edge of an anterior and inferior margin of the mandible, and at least one side wall extending upwardly from the flat plate and sized and shaped to engage an outer edge of at least a mental foramen of the mandible when the flat plate straddles the lower edge of the mandible. The device further includes a tissue supporting element coupled to the anchor element and extending outwardly therefrom and adapted to be implanted within the tongue. When the anchor element is engaged with the mandible and the tissue supporting element implanted in the tongue, rearward movement of the tongue is resisted without mechanical fixation of the anchor element to the mandible.

The tissue supporting element may be a looped filamentary element, and may further be made of a material selected from the group consisting of polypropylene, ePTFE, polyamide, fibers produced from fluoropolymers, polyesters, polyolefins, urethanes, Poly (hexafluoropropylene-VDF) and polyaryletherketones.

The device may further include a clamp element coupled to the anchor element and adapated to fixedly secure the filamentary element thereto, which may further be removably coupled to the anchor element.

In yet another embodiment, the anchor element further includes first and second side walls extending upwardly from the plate-like element, wherein the first side wall is sized and shaped to engage one lateral outer edge of the mandible and the second side wall is sized and shaped to engage the opposite lateral outer edge of the mandible.

In yet another embodiment, the device further includes an adjustment mechanism for adjusting a position of the first and second side walls relative to the plate-like element.

Also provided is a device for treating obstructive sleep apnea in a human patient having a mandible and a tongue including an anchor element sized and shaped to abut at least two distinct non-coplanar surfaces of the mandible when implanted in the patient, and a tissue supporting element coupled to the anchor element and extending outwardly therefrom and adapted to be implanted within the tongue. When the device is implanted within the patient, the anchor element is held in engagement with the mandible solely through forces of the soft tissues opposing the abutting locations.

The present disclosure also provides a method for treating obstructive sleep apnea, including the steps of obtaining an implantable tissue supporting device having an anchor element including a plate-like element and first and second side walls extending upwardly from first and second sides thereof, and a soft tissue supporting element coupled to the anchor element and extending outwardly therefrom; and implanting the implantable tissue supporting device within a patient such that the anchor element straddles and engages the anterior and inferior margins of the mandible, and the soft tissue supporting element is implanted within the patient's tongue so as to prevent rearward movement of the tongue without mechanical affixation of the anchor element to the mandible.

The soft tissue supporting element may be a looped filamentary element.

The method may further include adjusting the position of the tissue supporting element relative to the anchor element, then fixedly securing the tissue supporting element to the anchor element.

Finally, another method is provided for treating obstructive sleep apnea including the steps of obtaining an implantable tissue supporting device including an anchor element and a soft tissue supporting element coupled to the anchor element and extending outwardly therefrom; implanting the anchor element so that it substantially abuts at least two distinct non-coplanar surfaces of a patient's mandible and has no further affixation to said mandible; and implanting the soft tissue supporting element within the patient's tongue so as to resist rearward motion of the tongue via engagement of the anchor element with the mandible.

These and other objects, features and advantages of the present invention will be apparent from the following detailed description of illustrative embodiments thereof, which is to be read in connection with the accompanying drawings.

DETAILED DESCRIPTION

Although the tissue supporting device will be described herein with particular reference to supporting or suspending the tongue from the mandible for the treatment of obstructive sleep apnea, it is to be understood that the present invention is not so limited and may have application for supporting or suspending soft tissue from other bony structures and/or for treating other medical conditions.

Figure 3:
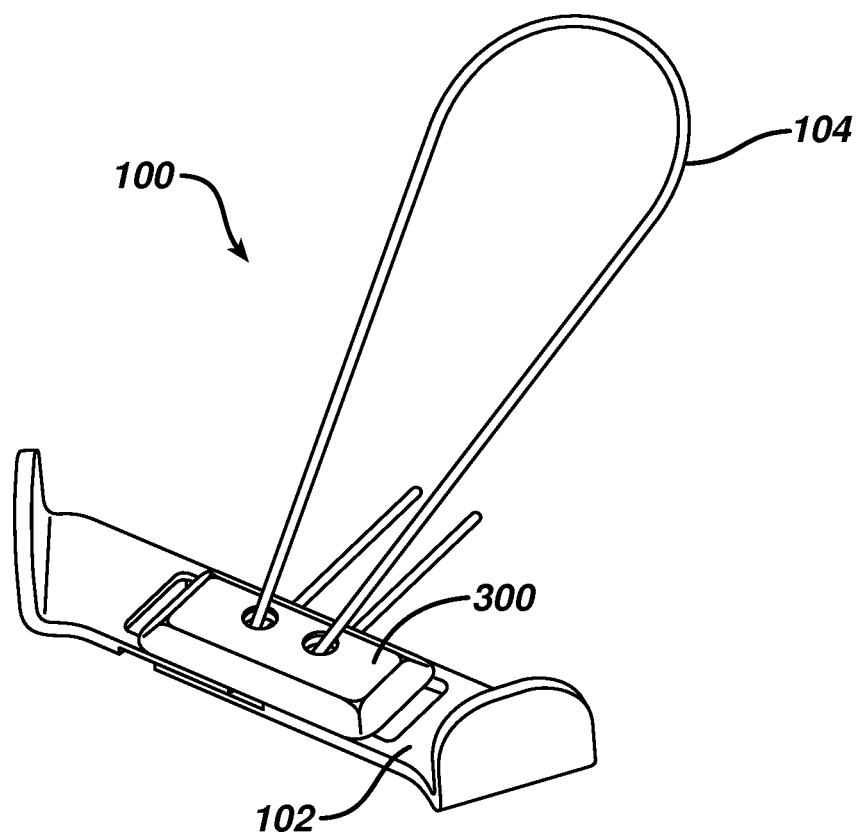
FIG. 3 is a perspective view of a tissue supporting device according to the present invention.
Figure 4:
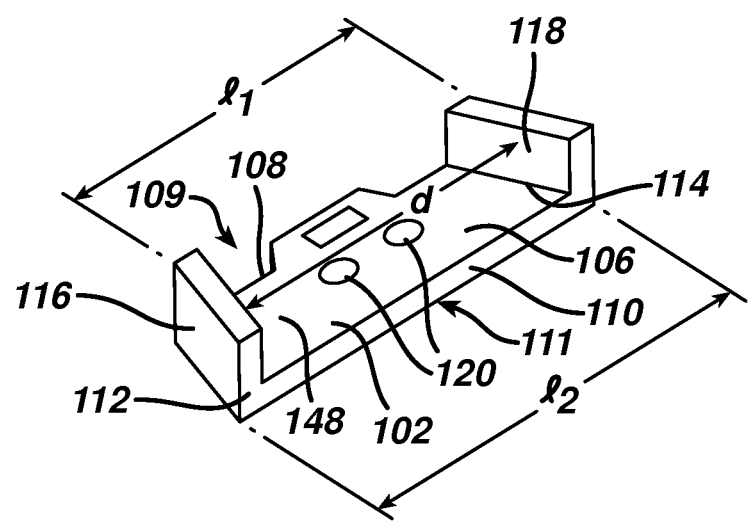
FIG. 4 is a perspective view of the anchor element of the embodiment of FIG. 3.

FIG. 3 illustrates one embodiment of a tissue supporting device according to the present invention. The tissue supporting device 100 includes an anchor element 102 and a soft tissue supporting element 104 coupled thereto. One embodiment of an anchor element 102 is shown in more detail in FIG. 4, and includes a plate-like element 106 which is defined by a front edge 108 at a front side 109, a rear edge 110 at a rear side 111, and first and second side edges 112, 114. The front edge 108 has a length $l_1$ that is shorter than the length $l_2$ of the rear edge 110. While the particular embodiment discloses a substantially flat plate-like element 106, the plate-like element may be produced with a stepped or contoured surface that fits within the infra-mandibular cavity, thereby more closely approximating the distal surface of the digastric and mylohyoid muscles. When fabricated in this manner, the final location of the suspension loop anchor point may more closely simulate the insertion point at the genial tubercle on the lingual surface of the mandible. The use of the stepped anchor more closely approximates the natural angle of suspension provided by the geniohyoid and genioglossus musculature. For sake of clarity, the term "plate-like element" as used herein encompasses any such embodiments. The anchor element 102 also includes at least one side wall, and preferably first and second side walls 116, 118. The first and second side walls 116, 118 extend upwardly from the plate-like element 106, and are substantially aligned along the first and second side edges 112, 114 of the plate-like element. The first and second side wall elements extend along two distinct, non-connected planes, that extend outward from a remote convergence point. Although in the illustrated embodiment the first and second side walls extend substantially along the entire length of the first and second side edges of the plate-like element, the side walls may extend along any portion of the length. Additionally, while the first and second side walls are illustrated as flat planar structures, it is envisioned that the side walls may have a three dimensional, non-planar form that is contoured to the features of the receiving mandibular surface, and the term "side walls" as used herein is intended to cover any such embodiments. The distance d between the first and second side walls increases from the front side 109 to the rear side 111 of the plate-like element so as to form a V-like shape as illustrated in FIG. 4, the importance of which will be described further below.

In the illustrated embodiment, the plate-like element further includes one or more apertures 120 therethrough, and in a preferred embodiment the soft tissue supporting element 104 is a filamentary or fiber-like element such as non-absorbable surgical suture, which is coupled to the anchor element by threading through the one or more apertures. Materials that are suitable for use as a soft tissue supporting element include, polypropylene, ePTFE, polyamide, fibers produced from fluoropolymers, polyesters, polyolefins, urethanes, Poly (hexafluoropropylene-VDF) and polyaryletherketones.

Figure 5:
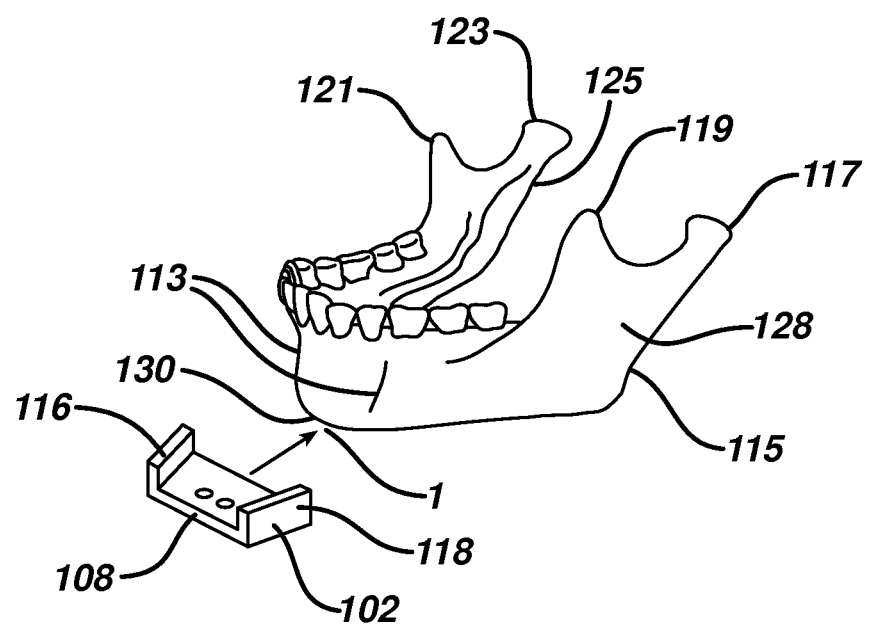
FIG. 5 illustrates the anchor element of FIG. 4 in relation to a human mandible.
Figure 6:
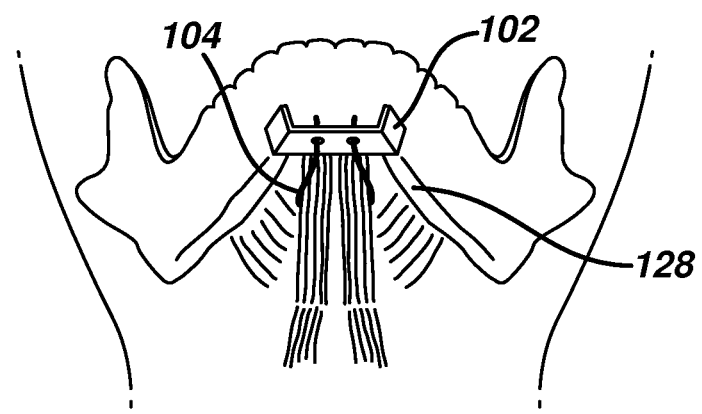
FIGS. 6-8 are an inferior view, saggital view, and lateral view respectively of a tissue supporting device of the present invention relative to the human anatomy.
Figure 11A:
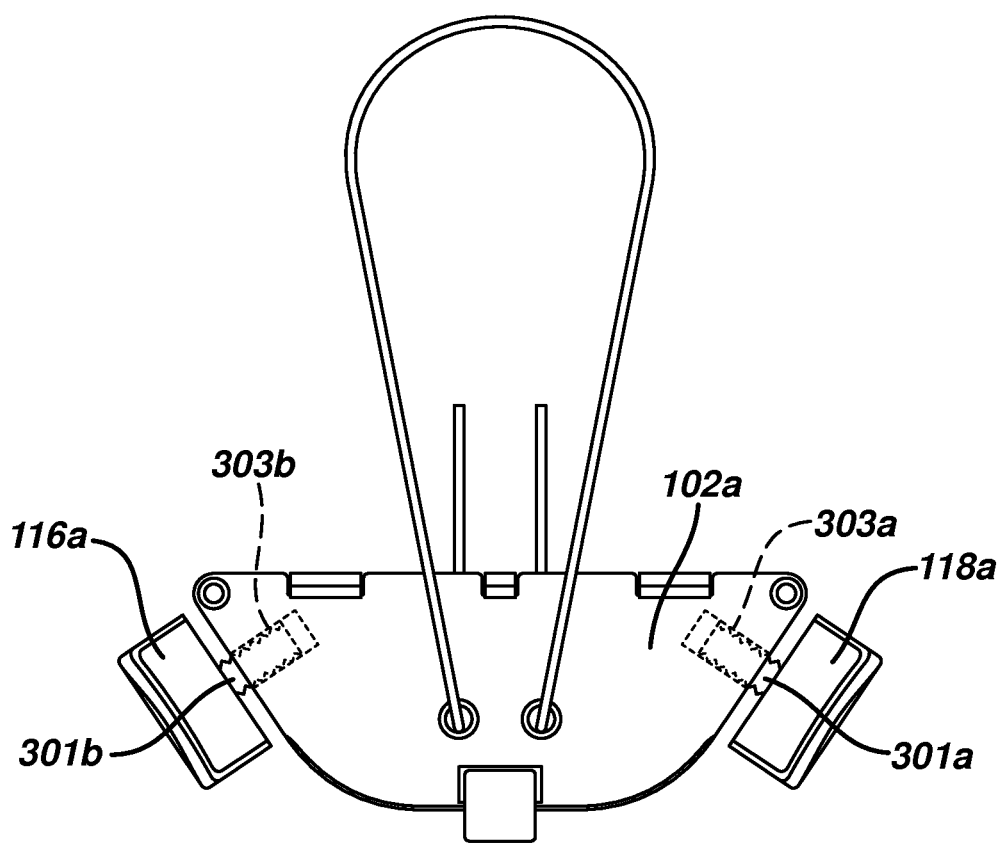
FIGS. 11a and 11b illustrate a tissue supporting device according to the present invention including adjustability features.
Figure 11B:
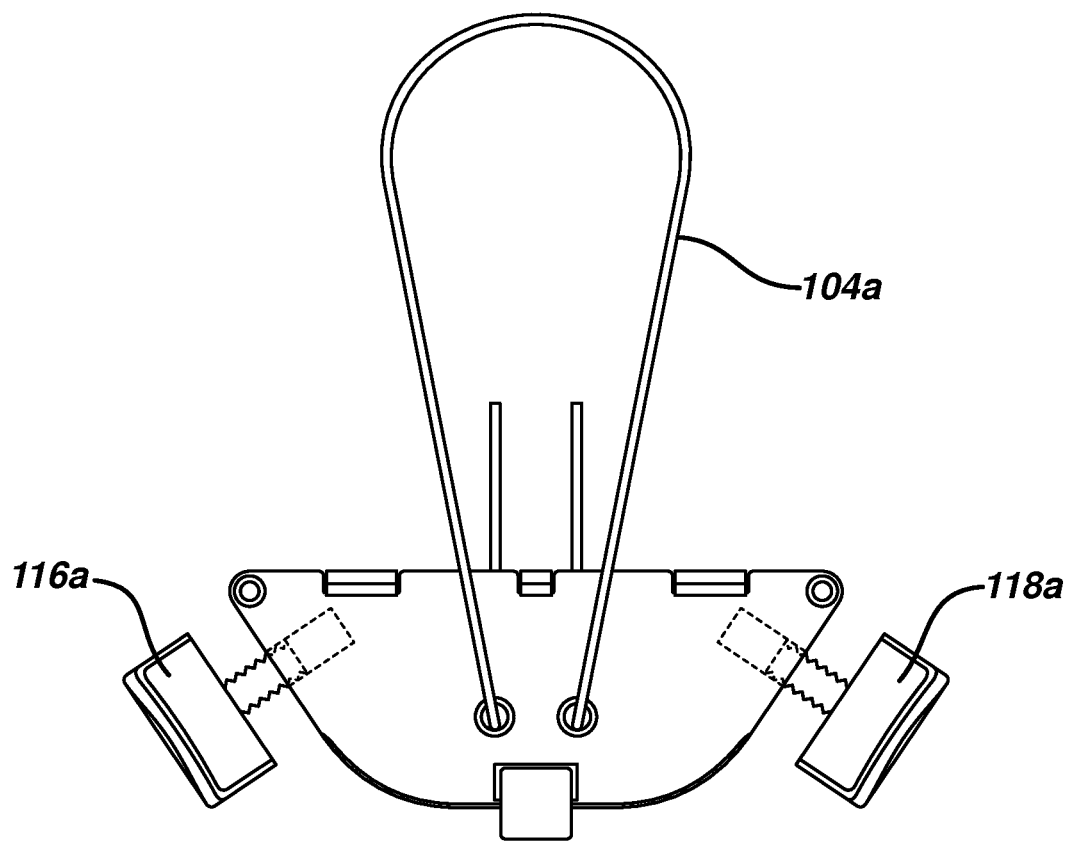

FIGS. 5-8 illustrate use of the device of the present invention for treating obstructive sleep apnea. FIG. 5 illustrates a mandible 128 of a patient, with the anchor element 102 being positioned relative to the anterior and inferior margin of the mandible such that the front edge 108 of the anchor element is closest to the front edge 130 of the mandible. It should be noted that the shape of the device approximates the somewhat planar configuration of the mandible. The mandible 128 is comprised essentially of three main planar like elements that converge at various angles along a central line of symmetry. While the surface texture and contours of the mandible are somewhat irregular or non-planar, the broad mandibular surfaces can be considered as approximately planar in a general form. The first vertical plane is located along the anterior face of the mandible and extends to the approximate location of the mentalis 113 near the incisive fossa on the exterior surface of the mandible. The first vertical plane is connected at an oblique angle to the two vertical planes that form the lateral surfaces of the mandible. The first vertical pane is roughly defined as extending approximately from the right side of the mentalis 113 to the right ramus 125 extending upward to the level of the right condyle 123 and right coronoid process 121. The second vertical pane is roughly defined as extending approximately from the left side of the mentalis 113 to the left ramus 115 extending upward to the level of the left condyle 117 and left coronoid process 119. In this manner, given the v-like shape of the anchor element formed essentially by two distinct converging side wall plane elements and the corresponding converging planar shape of the mandible, the anchor element straddles and engages the mandible to provide a stable anchor for the soft tissue supporting element by the proximity to, or abutting to, similarly shaped non-coplanar surfaces of the mandible without requiring any mechanical fixation to the bone as will be further described below. It should be noted that while the anchor element 102 of the tissue supporting device 100 is disclosed as a monolithic component, it is envisioned that the structure may be made of modular type construction whereby the positioning of the side walls relative to the plate-like element is adjustable for a better custom fit through the use of segmented interlocking components or the like. For example, FIGS. 11a and 11b illustrate one embodiment where the first and second side walls 116a, 118a are movably coupled to the plate-like element 102a. Ribbed or ratcheted projections 301a, 301b that extends outwardly from the first and second side walls respectively, are received within and engage with corresponding slots 303a, 303b in the plate-like element 102a. This slotted and ribbed arrangement is produced with a series of latching positions that enable a finite number of interlocked positions. The device is placed similar to the monolithic formed device with the exception that the width of the device is adjusted to fit the width of the particular mandible by compressing the side walls and plate-like element together until the final locked position is reached that ensures optimal placement. In an alternate embodiment (not shown), the plate may be split into two halves, with each half having an "L" shaped profile formed by the side wall element and the partial lower plate. The lower plate portion includes a similar horizontal slot and rib arrangement that allows the two halves to be compressed together.

Figure 1:
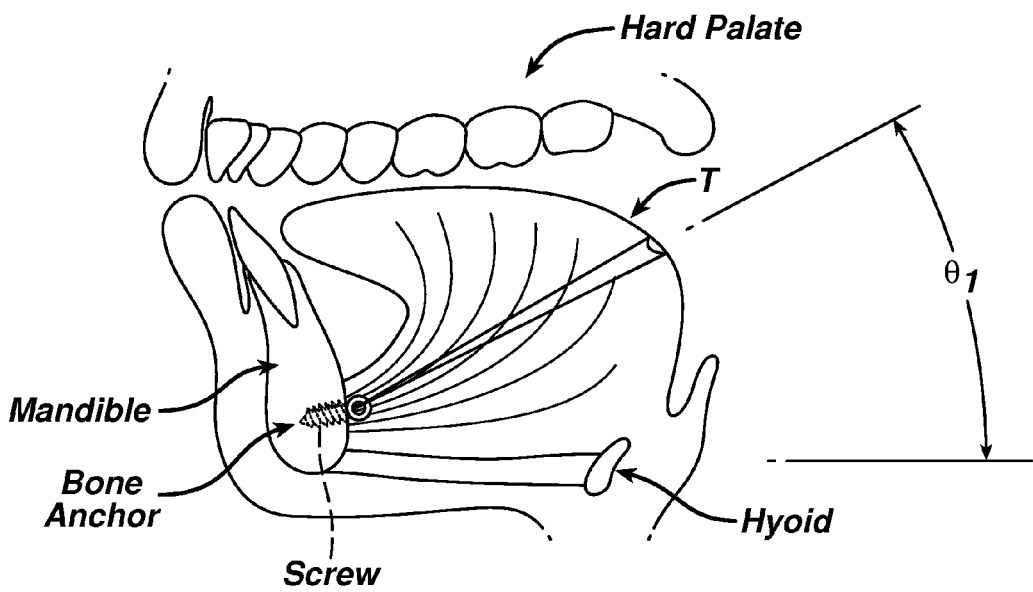
FIGS. 1 and 2 illustrate prior art tongue suspension devices.
Figure 2:
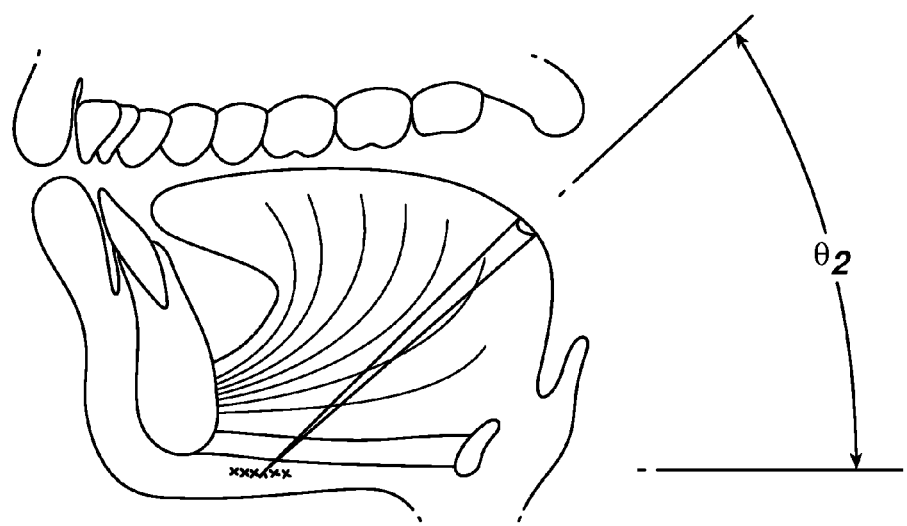
Figure 7:
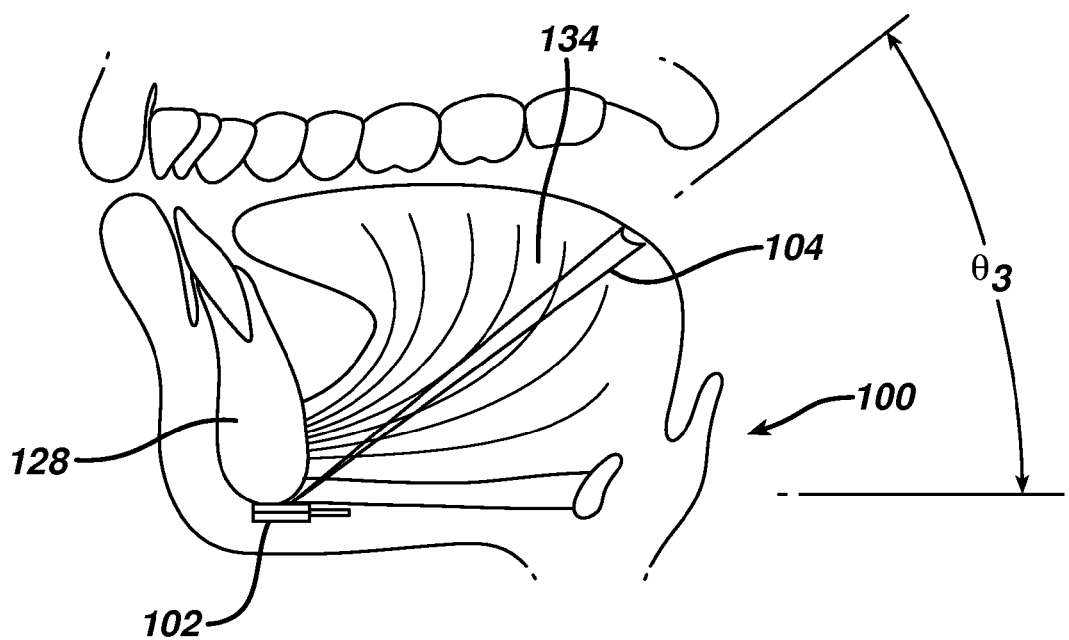
Figure 8:
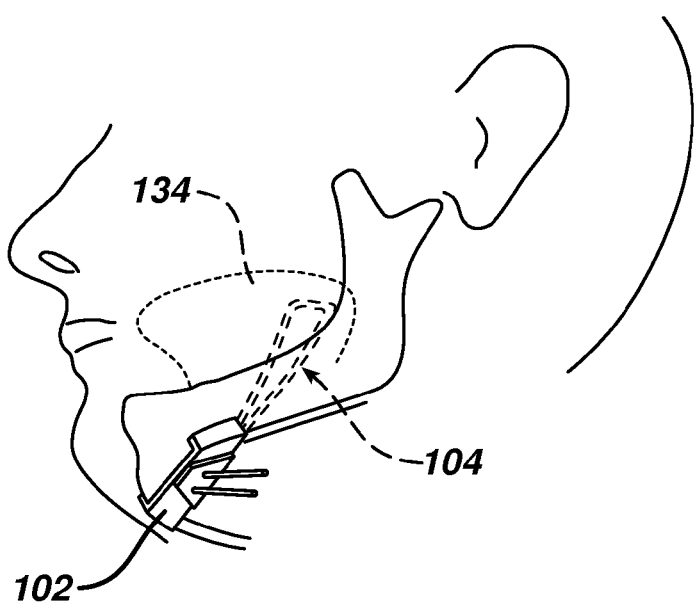

Referring now to FIGS. 7-8, the soft tissue supporting element 104 is adapted to engage and provide a tension element or to suspend the tongue from the anchor element in order to prevent rearward movement of the tongue that will occlude or partially occlude the upper airway. In the illustrated embodiment, the soft tissue supporting element is implanted within the tongue 134 and extends outwardly from the anchor element 102 to the submucosal tissues located approximately at the position of the circumvallate papillae and passes laterally across the tongue for a distance of 2 cm located approximately 1 cm lateral from the median sulcus portion of the tongue, at an angle θ that substantially corresponding to known bone anchor type suspension devices as shown in FIG. 1, and that place tensile force vectors on the anchor element that cause it to further engage with the mandible. Once engaged, rearward motion is resisted by the convergence of the side walls of the anchor element and elevating forces are resisted by the presence of the inferior surface of the mandible resulting in a compressive force at the interface of the anchor and mandible. As a result, the anchor element engages firmly with the mandible in a manner that will resist the loading of the soft tissue supporting element, but also in a manner that does not require mechanical fixation to the mandible as with the bone anchor devices of the prior art.

Figure 9:
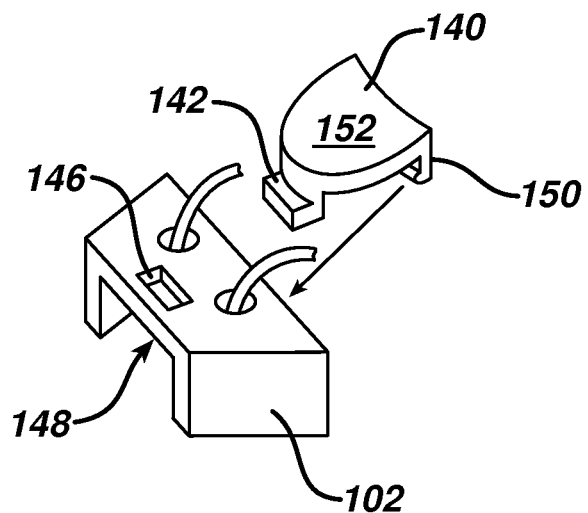
FIG. 9 illustrates a tissue supporting device according to the present invention including an additional clamp.

The tissue supporting device may further include a clamp, cover or the like that engages or clamps the soft tissue supporting element to the anchor element. FIG. 9 illustrates one such clamp element 140 designed to engage the anchor element 102 in such a manner that the ends of the soft tissue supporting element 104 are clamped or otherwise fixedly secured between the clamp element and anchor element. In the illustrated embodiment, the clamp element 140 includes a first projection 142 extending outwardly therefrom that is sized and shaped to pass through a corresponding opening 146 through the anchor element and also engage a top surface 148 of the plate-like element. The clamp element 140 further includes a second projection 150 sized and shaped to engage the rear edge 110 of the anchor element once the first projection is engaged, to thereby form a snap fit between the elements such that the base 152 of the clamp firmly engages the soft tissue supporting element between the clamp and anchor element.

Figure 12A:
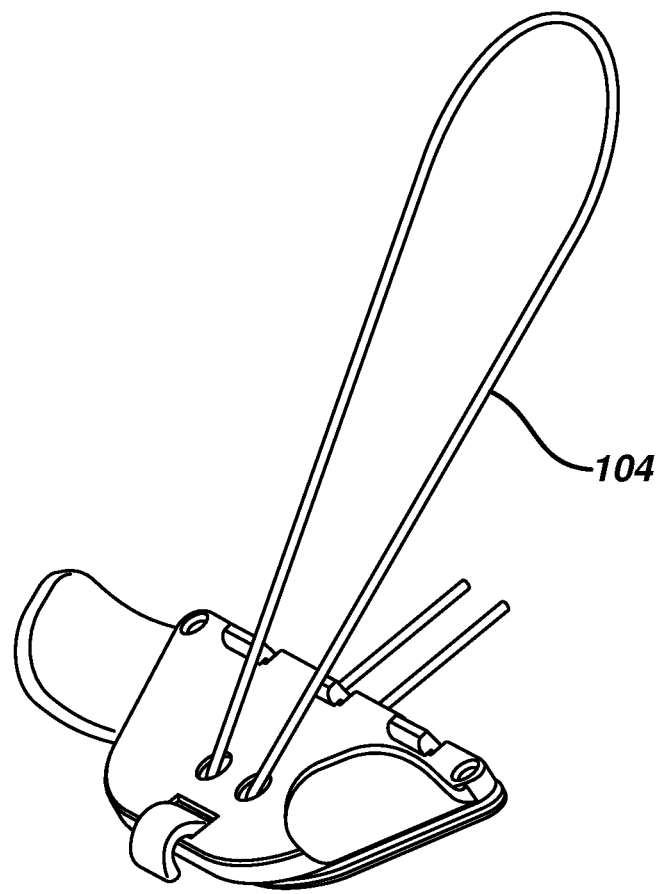
FIGS. 12a and 12b illustrate an alternate embodiment of a tissue supporting device including a clamping feature.
Figure 12B:
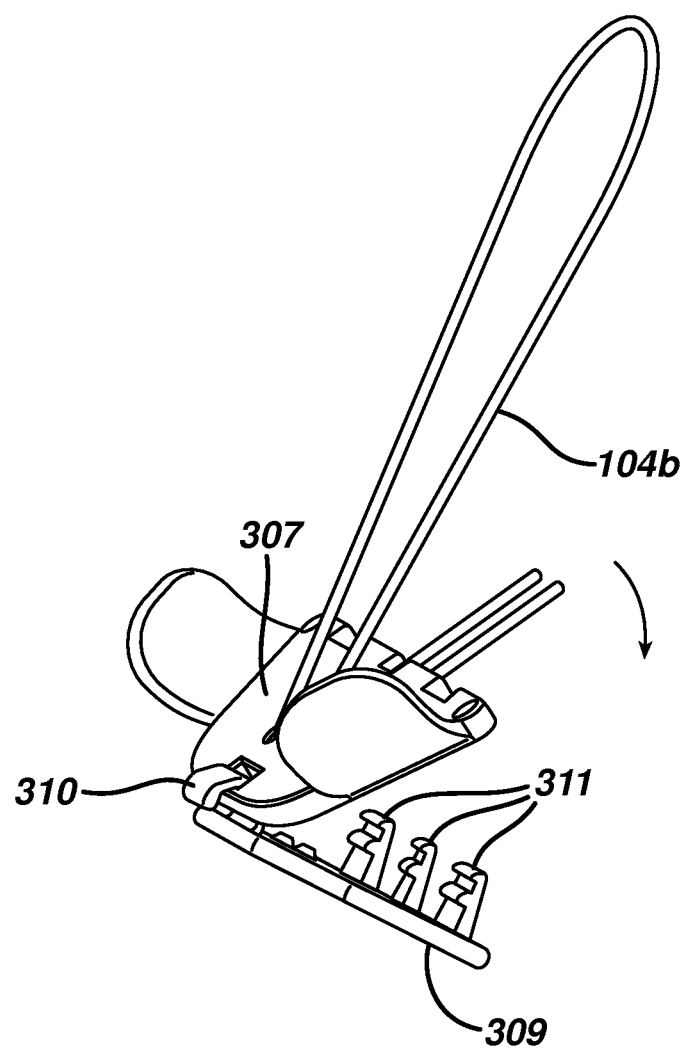

FIGS. 12a and 12b illustrate an alternate embodiment having first and second plate-like elements 307, 309 that snap together to fixedly secure the tissue supporting element 104 therebetween. The first and second plate-like elements 307, 309 are coupled together at a front side by any suitable hinge mechanism 310. The rear side includes one or more projections 311 sized and shaped to provide a snap-lock fit that fixedly engages the first and second plate-like elements 307, 309 together when the first plate-like element is pivoted downward as shown by the arrow in FIG. 12b. Although particular embodiments are described herein, those skilled in the art will readily recognize various other clamping mechanisms that may be used in connection with the present invention. Further, the interlocking features of the clamp and the anchor may be produced as a series of snap locks. The use of multiple snap locks enable a graduated increase in the clamping force applied to the fiber. The graduated tensioning allows for initial positioning of the fiber through the application of a low frictional force created through closure of the clamp component into its first position. Once the soft tissue support device has been positioned correctly, the clamp is snapped into a second position that provides the final locking force for the soft tissue supporting element. Alternatively, while the anchor device as illustrated discloses a simple interlocking clamp feature, the device may alternatively be produced with adjustable tensioning devices such as screw driven slides, ratchets, and wedge clamps.

The additional clamp element may allow for post surgical adjustments by further access to and disengaging of the clamp element, pulling on the soft tissue supporting elements to provide greater support or suspension, and re-engaging or re-clamping the clamp to fixedly secure the soft tissue supporting elements to the anchor element in the increased suspension state.

Figure 10:
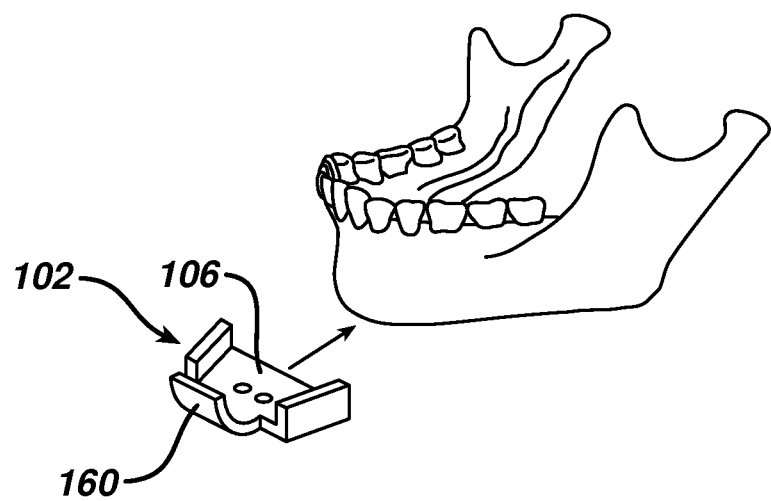
FIG. 10 illustrates an alternate embodiment of an anchor element of the tissue supporting device of the present invention.
Figure 13:
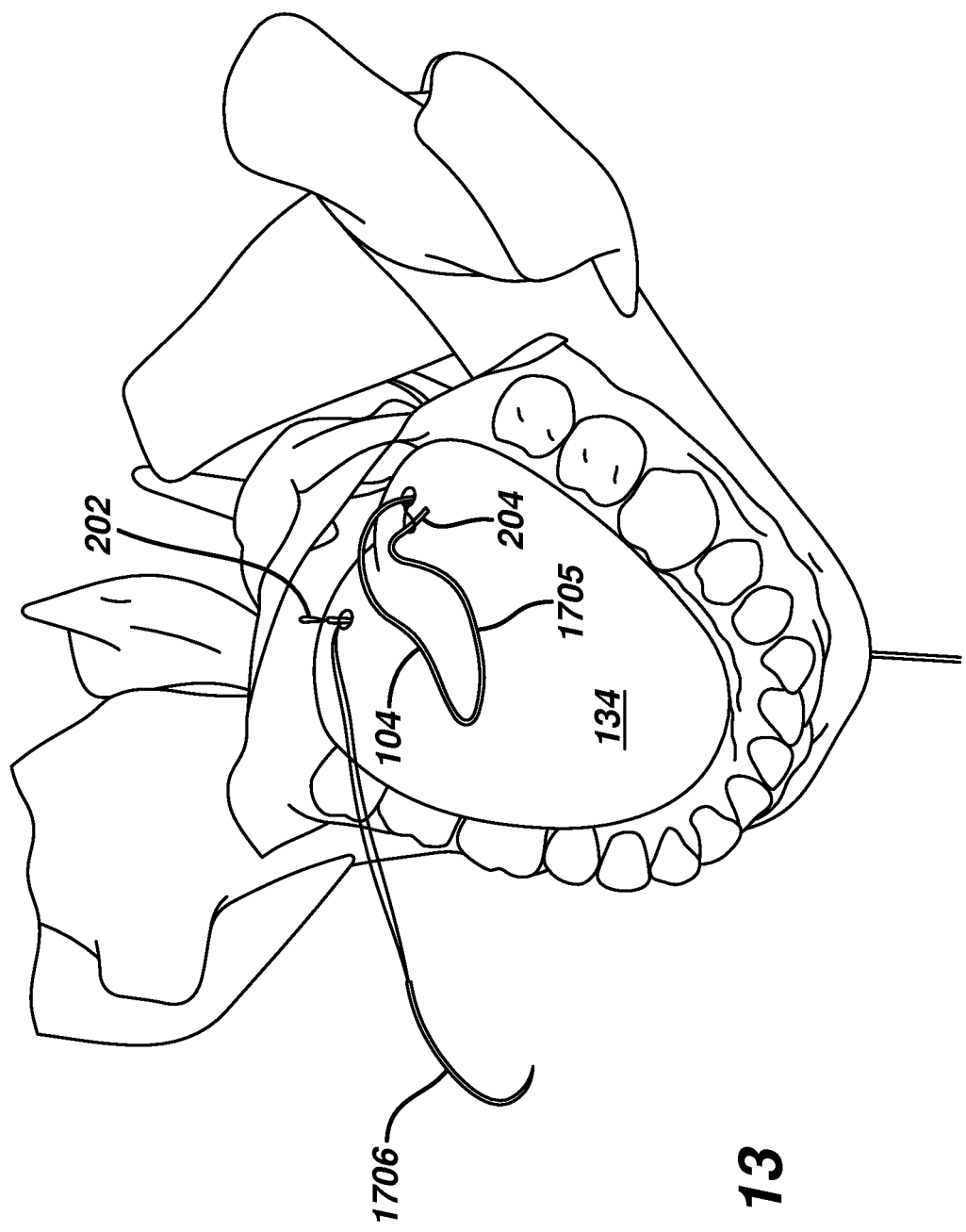
FIG. 13 illustrates an exemplary implantation technique for implanting the tissue supporting element.

In order to implant the device, an incision is made in the inferior region of the mandible, slightly posterior to the mental protuberance. A pocket is created to receive the anchor element through the dissection of the tissues away from the inferior surface of the mandible. The soft tissue supporting element may be placed within the tongue through the use of trocars and snare-like elements similar to those described in U.S. Patent Publication No. 2010/0137905, which is incorporated herein by reference in its entirety. According to one technique, the fiber is placed laterally through the tongue through the use of a pre-attached needle or through the use of a curved eyed needle or snare element. The needle is passed laterally from approximately 1 cm off from the median sulcus to approximately 1 cm lateral to the opposite side of the median sulcus at the location of the circumvallate papillae. The fiber is passed approximately 1-2 mm below the surface of the mucosa of the tongue. After the initial fiber placement has been completed, approximately 10-12 cm of the free ends of the soft tissue support element are extending from the surface of the tongue within the oral cavity. Snare type needles 202 are then passed from the inferior incision in the sub-mental region, through the tongue and exits through the same punctures as the free ends of the soft tissue supporting element as shown in FIG. 13. The respective free ends 204 of the soft tissue supporting element 104 are placed in the snare device 202 and are pulled though the tissues of the tongue to the exit point and hole 120 within the anchor device 102. The free ends of the soft tissue supporting element are tensioned slightly and tied together, or a clamp element 140 is used to lock the free ends of the tissue supporting element in position. The incisions are then closed through standard techniques.

Where increased holding strength of the anchor element is desired, the anchor element may further include an anterior projection element 160 that projects upwardly from the front side 109 of the flat plate 106 of the anchor element 102 to provide a distinct stop against the front of the mandible as shown in FIG. 10. This may be particularly useful for patients with very narrow mandibles.

The anchor element may be comprised of a solid, biocompatible material, or may be a composite structure that can increase tissue incorporation or integration and device compliance. For example, materials such as mesh materials, foams, porous surface treatments or perforations may be added to improve tissue ingrowth to a solid rigid structure. Alternatively, the anchor device, in the simple design providing a tying location for the soft tissue supporting element, may be produced as a laminated structure that combines absorbable polymeric or metallic materials such as PGA, polydioxanone, magnesium, etc with non-absorbable textile materials such as polypropylene, PVDF, polyesters, polyelefins, eptfe, metallic textiles such as stainless steel or titanium etc. or combinations thereof. In this particular embodiment, the device is rigid at the time of implantation to ensure placement without fixation. As the absorbable materials are removed over time, the textile structure integrates with the surrounding tissues and the implant becomes flexible to enable some additional degree of free motion to the soft tissue supporting element.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A device for treating obstructive sleep apnea in a human patient having a mandible and a tongue comprising:
   an anchor element having a plate-shape element adapted to be implanted in said patient and sized and shaped to straddle a lower edge of an anterior and inferior margin of the mandible of said patient, and at least one side wall extending upwardly from the flat plate and sized and shaped to engage an outer edge of at least a mental foramen of the mandible of said patient when the flat plate straddles the lower edge of the mandible; and
   a looped, flexible filamentary element coupled to the anchor element and extending outwardly therefrom and adapted to be implanted within the tongue, the looped filamentary element having a length sufficient to extend outwardly from the anchor element to the submucosal tissue substantially at the position of the circumvallate papillae, laterally across the tongue a predetermined distance, and back through the tongue to the anchor element;
   wherein when the anchor element is engageable with the mandible and the tissue supporting element implantable in the tongue, rearward movement of the tongue is resisted without mechanical fixation of the anchor element to the mandible.

2. The device according to claim 1, wherein the looped filamentary element is comprised of a material selected from the group consisting of polypropylene, ePTFE, polyamide, fibers produced from fluoropolymers, polyesters, polyolefins, urethanes, Poly(hexafluoropropylene-VDF) and polyaryletherketones.

3. The device according to claim 1, further comprising a clamp element coupled to the anchor element and adapted to fixedly secure the filamentary element thereto.

4. The device according to claim 3, wherein the clamp element is removably coupled to the anchor element.

5. The device according to claim 1, wherein the anchor element further comprises first and second side walls extending upwardly from the plate-like element, wherein the first side wall is sized and shaped to engage one lateral outer edge of the mandible and the second side wall is sized and shaped to engage the opposite lateral outer edge of the mandible.

6. The device according to claim 1, further comprising an adjustment mechanism for adjusting a position of the first and second side walls relative to the plate-like element.

* * * * *